United States Patent
Vogt et al.

(10) Patent No.: US 10,322,207 B2
(45) Date of Patent: Jun. 18, 2019

(54) ANTISEPTIC POLYMETHYLMETHACRYLATE BONE CEMENT

(71) Applicant: HERAEUS MEDICAL GMBH, Wehrheim (DE)

(72) Inventors: Sebastian Vogt, Erfurt (DE); Lorena Calderón Ortiz, Frankfurt am Main (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 0 days.

(21) Appl. No.: 15/637,456

(22) Filed: Jun. 29, 2017

(65) Prior Publication Data

US 2018/0000984 A1 Jan. 4, 2018

(30) Foreign Application Priority Data

Jul. 4, 2016 (DE) .................. 10 2016 212 091

(51) Int. Cl.
| | |
|---|---|
| *A61L 24/04* | (2006.01) |
| *A61L 24/06* | (2006.01) |
| *C07C 409/24* | (2006.01) |
| *C08F 220/18* | (2006.01) |
| *A61L 24/00* | (2006.01) |
| *A61K 33/40* | (2006.01) |
| *C08L 33/12* | (2006.01) |
| *C08F 212/08* | (2006.01) |

(52) U.S. Cl.
CPC .............. *A61L 24/04* (2013.01); *A61K 33/40* (2013.01); *A61L 24/0015* (2013.01); *A61L 24/0073* (2013.01); *A61L 24/06* (2013.01); *C07C 409/24* (2013.01); *C08F 220/18* (2013.01); *C08L 33/12* (2013.01); *A61L 2300/212* (2013.01); *A61L 2430/02* (2013.01); *C08F 212/08* (2013.01); *C08L 2312/00* (2013.01)

(58) Field of Classification Search
USPC ................. 523/116, 117; 433/228.1; 106/35
See application file for complete search history.

(56) References Cited

U.S. PATENT DOCUMENTS

| | | | | |
|---|---|---|---|---|
| 3,234,194 A | * | 2/1966 | Slocum ..................... C08F 4/32 | 524/336 |
| 3,827,933 A | * | 8/1974 | Duggins et al. ......... C04B 26/06 | 428/220 |
| 4,588,583 A | | 5/1986 | Pietsch et al. | |
| 4,650,612 A | * | 3/1987 | Dankowski ........... C07C 409/24 | 502/159 |
| 4,849,223 A | | 7/1989 | Pratt et al. | |
| 4,866,146 A | | 9/1989 | Janda et al. | |
| 6,984,392 B2 | | 1/2006 | Bechert et al. | |
| 8,512,762 B2 | | 8/2013 | Vogt et al. | |
| 8,598,251 B2 | | 12/2013 | Vogt et al. | |
| 8,791,172 B2 | | 7/2014 | Vogt et al. | |
| 8,801,967 B2 | * | 8/2014 | Mack ..................... C04B 18/022 | 252/301.33 |
| 9,144,626 B2 | | 9/2015 | Vogt et al. | |
| 9,387,275 B2 | | 7/2016 | Vogt et al. | |
| 9,700,649 B2 | | 7/2017 | Vogt | |
| 2003/0165556 A1 | * | 9/2003 | Bechert ............... A61L 24/0015 | 424/423 |
| 2006/0018943 A1 | | 1/2006 | Bechert et al. | |
| 2006/0135643 A1 | * | 6/2006 | Klee ..................... A61K 6/0017 | 523/116 |
| 2006/0275339 A1 | | 12/2006 | Schilke et al. | |
| 2009/0010981 A1 | | 1/2009 | Bechert et al. | |
| 2009/0105144 A1 | | 4/2009 | Vogt et al. | |
| 2009/0105366 A1 | | 4/2009 | Vogt et al. | |
| 2010/0159027 A1 | | 6/2010 | Vogt et al. | |
| 2011/0183932 A1 | | 7/2011 | Vogt et al. | |
| 2011/0313078 A1 | | 12/2011 | Vogt et al. | |
| 2014/0141097 A1 | | 5/2014 | Vogt et al. | |
| 2014/0303275 A1 | | 10/2014 | Vogt et al. | |
| 2015/0290355 A1 | | 10/2015 | Vogt | |

FOREIGN PATENT DOCUMENTS

| | | |
|---|---|---|
| DE | 32 45 956 A1 | 6/1984 |
| DE | 37 30 921 A1 | 3/1989 |
| DE | 195 08 827 A1 | 9/1996 |
| DE | 198 08 962 C2 | 3/2002 |
| DE | 10 2007 052 116 A1 | 4/2009 |
| DE | 10 2007 050 762 B3 | 5/2009 |

(Continued)

OTHER PUBLICATIONS

Kühn, "PMMA Cements", Springer-Verlag Berlin Heidelberg, 2014.
German Office Action issued in corresponding application dated Mar. 3, 2017, 2017.
Data Sheet for ethylene glycol dimercaptoacetate, Sigma-Aldrich catalog, obtained on the website sigmaaldrich.com/catalog on Dec. 17, 2018.
Hazard and Precautionary Statements explanation of GHS07 safety designation, obtained on the website sigmaaldrich.com/help on Dec. 17, 2018.

*Primary Examiner* — Tae H Yoon

(74) *Attorney, Agent, or Firm* — Norris McLaughlin, P.A.

(57) ABSTRACT

An antiseptic composition for use as bone cement, in particular an antiseptic polymethylmethacrylate bone cement. The composition can be cured and comprises a pharmacologically tolerable salt of a monoperoxy dicarboxylic acid, whereby the salt of the monoperoxy dicarboxylic acid can be dissolved from the composition in the presence of water. Preferably, the salt of the monoperoxy dicarboxylic acid in the composition is used in the form of a powder, whereby the powder has a mean particle size of not more than 250 μm. Preferably, the salt of the monoperoxy dicarboxylic acid, in solution at room temperature, is not degraded within 5 min by the catalase enzyme.

24 Claims, No Drawings

(56) References Cited

FOREIGN PATENT DOCUMENTS

| | | |
|---|---|---|
| DE | 10 2008 030 312 A1 | 1/2010 |
| DE | 10 2009 005 534 B3 | 4/2010 |
| DE | 10 2010 005 956 A1 | 7/2011 |
| DE | 10 2010 024 653 A1 | 12/2011 |
| DE | 10 2012 022 419 A1 | 5/2014 |
| DE | 10 2014 105 267 A1 | 10/2015 |
| EP | 1 313 518 A1 | 5/2003 |
| EP | 1 648 531 A1 | 4/2006 |
| WO | 82 01990 A1 | 6/1982 |
| WO | 02 17984 A1 | 3/2002 |
| WO | 2005 009495 A1 | 2/2005 |

\* cited by examiner

ANTISEPTIC POLYMETHYLMETHACRYLATE BONE CEMENT

This application claims priority of German Patent Application No. DE 10 2016 212 091.3, filed Jul. 4, 2016, the entire contents of which are incorporated herein by reference.

The invention relates to a composition for use as a bone cement, in particular an antiseptic polymethylmethacrylate bone cement, whereby the composition can be cured and the composition comprises a pharmacologically tolerable salt of a monoperoxy dicarboxylic acid and the salt of the monoperoxy dicarboxylic acid can be dissolved from the composition in the presence of water. Moreover, the invention relates to a kit for use as a bone cement, in particular an antiseptic polymethylmethacrylate bone cement, whereby the kit comprises a paste A and a paste B, whereby at least one of the pastes A and/or B contains, as a component, a pharmacologically tolerable salt of a monoperoxy dicarboxylic acid. The invention further relates to a kit comprising a powder component C and a liquid monomer component D, whereby powder component C contains, as a component, a pharmacologically tolerable salt of a monoperoxy dicarboxylic acid.

Polymethylmethacrylate bone cements have been in use in orthopaedics and trauma surgery for decades for permanent mechanical fixation of total particular endoprostheses. These are based on powder-liquid systems, whereby it is customary to use methylmethacrylate as monomer. A general overview is provided in: K.-D. Kühn, PMMA Cements, Springer-Verlag Berlin Heidelberg 2014.

Aside from the powder-liquid cements, polymethylmethacrylate bone cements based on the use of cement pastes have also been proposed. DE 10 2007 052 116 A1 relates to a one-component bone cement. DE 32 45 956 A1, DE 10 2007 050 762 B3, and DE 10 2008 030 312 A1 describe two-component bone cements made of two cement pastes that are stored separately in suitable cartridges. Said pastes always contain one methacrylate monomer and at least one polymer dissolved therein. Moreover, said pastes can also contain cross-linked polymer particles that are insoluble in the methacrylate monomer. Both pasty components separately contain components of redox initiator systems that react only after the two pasty components are mixed and, in the process, form radicals, which initiate the radical polymerisation of the methacrylate monomer that leads to the curing of the mixed cement dough.

Currently, aside from agent-free polymethylmethacrylate bone cements, antibiotics-containing polymethylmethacrylate bone cements are used predominantly. Said bone cements contain the antibiotics, gentamicin sulfate or tobramycin sulfate, and are predominantly used for mechanical fixation of primary articular endoprostheses. Antibiotic bone cements aimed for mechanical fixation of revision articular endoprostheses often use combinations of antibiotics such as gentamicin sulfate and clindamycin hydrochloride as well as vancomycin hydrochloride and gentamicin sulfate.

There has been a number of attempts to incorporate antiseptics instead of antibiotics into polymethylmethacrylate bone cements.

WO 82/01990 A1 proposes a bone cement that contains up to 5% by weight silver salts. An antimicrobial composition containing up to 10% by weight elemental silver and, in addition, titanium dioxide or tantalum oxide is proposed in U.S. Pat. No. 4,849,223 A.

EP 1 313 518 A1 described a bone cement that contains silver particles of 20 μm in size. Said silver particles are made up of smaller silver particles of a size in the nanometre range. The use of elemental silver or silver salts is an issue since the silver ions, which are actually meant to act microbicidal, are non-selective and interact not only with microbial structures, but with human tissue structures as well. Accordingly, poorly water-soluble salts can be formed with cysteine and cysteine-containing proteins. Moreover, silver ions can react with phosphate ions to form poorly soluble silver orthophosphate. It must be presumed that silver compounds introduced into the human body can basically not be eliminated, as is evident from the long-known phenomenon of argyrosis, i.e., irreversible skin changes due to silver. EP 1 648 531 A1 disclosed a polymethylmethacrylate bone cement containing cationic antiseptics, whereby the antiseptic polyhexamethylenebiguanide is particularly preferred. However, an issue to be discussed in this context is that said cationic antiseptics cannot be degraded by human tissue and there is a risk of local accumulation.

DE 10 2012 022 419 A1 proposes an antiseptic polymethylmethacrylate bone cement that contains hydrogen peroxide-releasing adducts, such as urea peroxide, or hydrogen peroxide-releasing salts, such as calcium peroxide. Hydrogen peroxide is released by the action of water or aqueous solutions on the cured polymethylmethacrylate bone cement. An antiseptic effect is evident only right at the surface of the bone cement, since the released hydrogen peroxide is decomposed by the catalase enzyme (EC 1.11.1.6) within a short period of time after contact with body fluid.

The invention is based on the object to devise a composition for use as bone cement, in particular as polymethylmethacrylate bone cement, which, after implantation, releases a broadly effective antiseptic at the surface of the bone cement by the action of body fluids, whereby the antiseptic is to temporarily prevent microbial colonisation of the cement surface. It is therefore another object of the invention to devise a composition for use as bone cement, in particular as polymethylmethacrylate bone cement, that provides an antiseptic that is not degraded by the catalase enzyme within just a few minutes. It is therefore another object of the invention to devise a composition for use as bone cement, in particular as polymethylmethacrylate bone cement, that provides an antiseptic that does not interfere with the radical polymerisation during the curing of the bone cement The antiseptic bone cement needs to meet the requirements of ISO 5833, i.e., compressive strength ≥70 MPa, flexural strength ≥50 MPa, and flexural modulus ≥1800 MPa. It is another object of the invention to devise a composition for use as bone cement, in particular as polymethylmethacrylate bone cement, that is characterised by a combination of the aforementioned features.

The independent claims make a contribution to meet, at least partially, at least one of the objects specified above. The dependent claims are preferred embodiments that contribute to meeting, at least partially, at least one of the objects.

A contribution to meeting at least one of the objects according to the invention is made by an embodiment 1 of a composition for use as bone cement, whereby the composition can be cured and the composition comprises a pharmacologically tolerable salt of a monoperoxy dicarboxylic acid and the salt of the monoperoxy dicarboxylic acid can be dissolved from the composition in the presence of water.

It has been evident, surprisingly, that pharmacologically tolerable salts of monoperoxy dicarboxylic acids that are being dissolved or can be dissolved from cured bone cements, in particular polymethylmethacrylate bone cements, by the action of aqueous solutions show a long-lasting antiseptic effect at the cement surface.

According to the invention, the monoperoxy dicarboxylic acid can be dissolved from the composition, preferably after a curing process, such as by polymerisation of a liquid monomer and at least one organic polymer that is soluble in said monomer.

Free monoperoxy dicarboxylic acids are usually unstable compounds, which, for this reason, are used in the form of stable and pharmacologically tolerable and/or pharmacologically acceptable metal salts in the scope of the invention. Examples of pharmacologically tolerable and/or acceptable salts include alkali metal salts, in particular sodium, potassium, and lithium salts. Moreover, they are salts of alkaline earth metals, in particular magnesium and calcium salts, and the salts of some transition metals, in particular iron, zinc, and copper salts.

A monoperoxy dicarboxylic acid shall be understood to be a dicarboxylic acid with two carboxyl groups, in which one of the two carboxyl groups is present in oxidised form as a peroxycarboxyl group.

Preferably, the monoperoxy dicarboxylic acid according to the invention comprises at least 4 carbon atoms.

The monoperoxy dicarboxylic acids are, in particular aliphatic unbranched or branched monoperoxy dicarboxylic acids with 4 to 20 carbon atoms, alicyclic monoperoxy dicarboxylic acids with 8 to 12 carbon atoms, aromatic monoperoxy dicarboxylic acids with 8 to 12 carbon atoms or a mixture comprising at least 2 of said monoperoxy dicarboxylic acids.

Examples of aliphatic and alicyclic monoperoxy dicarboxylic acids include monoperoxy succinic acid, monoperoxy glutaric acid, monoperoxy adipic acid, monoperoxy cyclohexyldicarboxylic acid, monoperoxy pimelic acid, monoperoxy suberic acid, monoperoxy azelaic acid, monoperoxy sebacic acid, monoperoxy nonanedicarboxylic acid, monoperoxy decanedicarboxylic acid, monoperoxy undecanedicarboxylic acid, and monoperoxy dodecanedicarboxylic acid, whereby monoperoxy glutaric acid, monoperoxy succinic acid, and monoperoxy cyclohexyldicarboxylic acid are particularly preferred.

Examples of aromatic monoperoxy dicarboxylic acids include monoperoxy phthalic acid, monoperoxy terephthalic acid, monoperoxy isophthalic acid, and monoperoxy naphthalic acid, whereby monoperoxy phthalic acid is particularly preferred.

Preferably, the pharmacologically tolerable or pharmacologically acceptable salts of the monoperoxy dicarboxylic acids have a free acid function, whereby the carboxyl group is present as protonated carboxylate and the peroxycarboxyl group as peroxycarboxylic acid group (—COOOH). The monoperoxy dicarboxylic acids therefore preferably form, with alkali metals, salts comprising one monoperoxy dicarboxylic acid in the salt and, with alkaline earth metals, alkaline earth metal salts with two monoperoxy dicarboxylic acids in the salt. The same applies accordingly to transition metal salts, depending on the position of the transition metal in the periodic system and the preferred oxidation state of the pharmacologically tolerable and/or pharmacologically acceptable transition metal.

The pharmacologically tolerable or pharmacologically acceptable salts of the monoperoxy dicarboxylic acids can be dissolved from the composition according to the invention by the action of water. "Can be dissolved" in this context should be understood to mean that the monoperoxy dicarboxylic acid salt can be dissolved from the composition either partially or fully, whereby the monoperoxy dicarboxylic acid salt preferably can be dissolved fully from the composition.

According to the invention, "in the presence of water", shall be understood to mean that the composition can contact water in the form of an aqueous solution or a partly-aqueous solution or pure water. In summary, reference is made herein to an aqueous medium, which means that the solution contains water. Aqueous solutions shall be understood to be, in particular, salt-containing and/or buffered solutions, preferably human or animal body fluids.

In an embodiment 2 according to the invention, the composition is designed according to embodiment 1, whereby the composition is an antiseptic bone cement.

Exposed to the action of water or aqueous solutions, such as an aqueous medium on the inside of the body, monoperoxy dicarboxylic acids and the salts thereof release hydrogen peroxide in an equilibrium reaction while forming the corresponding dicarboxylic acid. Both the monoperoxy dicarboxylic acid and the hydrogen peroxide reaction product are antiseptics that have a strong microbiocidal effect based on their oxidising effect. It is particularly advantageous that hydrogen peroxide cannot accumulate in the human body, since human tissue contains enzymes from the class of the peroxidases (EC 1.11.1), in particular catalase (EC 1.11.1.6), that degrade hydrogen peroxide. Another advantage of the composition according to the invention or the bone cement according to the invention is that it prevents the formation of resistance by the micro-organisms which can happen with antibiotics-based therapies. Another advantage of the use according to the invention is the local antiseptic effect, since the afore-mentioned peroxidases, in particular catalase, can degrade the hydrogen peroxide formed.

In an embodiment 3 according to the invention, the composition is designed according to embodiment 1 for 2, whereby the composition is an antiseptic polymethylmethacrylate bone cement.

The term, polymethylmethacrylate bone cement, shall be understood to refer to conventional cements, in which a polymer powder component and a liquid monomer component are mixed to form a self-curing cement dough through radical polymerisation. This term also includes pasty polymethylmethacrylate bone cements, in which two separate pre-swelled cement pastes are mixed to produce a self-curing cement dough. Pertinent examples are specified in published patent applications DE 10 2007 050 762 B3, DE 10 2010 024 653 B4, and DE 10 2010 005 956 B4.

In an embodiment 4 according to the invention, the composition is designed according to any one of the embodiments 1 to 3, whereby the salt of the monoperoxy dicarboxylic acid is an alkaline earth salt or an alkali salt.

Alkali and alkaline earth salts of the monoperoxy dicarboxylic acids are characterised by high solubility and good pharmacological compatibility. Moreover, alkali and alkaline earth salts cannot change their oxidation state, which is in contrast to salts of transition metals. Ions of transition metals, for example $Cr^{3+}$ or $Co^{2*}$, can effect catalytic degradation of the monoperoxy dicarboxylic acids due to a change of the oxidation state and can thus impaired the antiseptic efficacy.

Moreover, it has been evident, surprisingly, that polymethylmethacrylate bone cement also meets the requirements of ISO 5833 concerning the mechanical properties if the cement contains pharmacologically tolerable salts of monoperoxy dicarboxylic acids, in particular alkaline earth and alkali salts of monoperoxy dicarboxylic acids. These salts surprisingly have no interfering impact on the radical polymerisation preceding during the curing of polymethylmethacrylate bone cements.

In an embodiment 5 according to the invention, the composition is designed according to any one of the embodiments 1 to 4, whereby the alkaline earth salt is a magnesium salt.

Magnesium salts of the monoperoxy dicarboxylic acids are characterised by particularly high solubility and excellent pharmacological compatibility.

In an embodiment 6 according to the invention, the composition is designed according to any one of the embodiments 1 to 5, whereby the salt of the monoperoxy dicarboxylic acid is not soluble in methylmethacrylate at room temperature.

It is particularly preferred for the salts of the monoperoxy dicarboxylic acids used in this context to not be soluble in methylmethacrylate at 23° C. The low solubility provides additional assurance that the monoperoxy dicarboxylic acid or the pharmacologically tolerable salt used in this context does not undergo undesired reactions with the components of the monomer component of the bone cement to be polymerised. By this means, the antiseptic effect of the monoperoxy dicarboxylic acid is maintained even if the monomer component of the bone cement is stored for extended periods of time.

The salts of the monoperoxy dicarboxylic acids shall be considered to be "not soluble" in methylmethacrylate if the solubility at 23° C. is less than or equal to 3 g of salt per litre of ready-made solution (3 g/l).

In an embodiment 7 according to the invention, the composition is designed according to any one of the embodiments 1 to 6, whereby the salt of the monoperoxy dicarboxylic acid in the composition is used in the form of a powder, whereby the powder has a mean particle size of not more than 250 μm.

Powders with a mean particle size in the range of 100 μm to 250 μm are used preferably. In powders with particle sizes in the specified range, the rate of release of the monoperoxy dicarboxylic acid salt from the composition, in particular from the bone cement, upon contact with an aqueous medium is optimal and the mechanical strength of the cured cement is adversely affected only to a minimal extent or not at all.

It has been evident, surprisingly, that monoperoxy dicarboxylic acid salts with particle sizes of no more than 250 μm do not have an adverse effect on the mechanical properties of the cured composition, in particular of a bone cement. In particular, the requirements of the ISO 5833 standard concerning the flexural strength, flexural modulus, and compressive strength are met.

Moreover, the mean particle size of the powder used in this context being small, i.e., the specific surface area being large, means that monoperoxy dicarboxylic acid salts that are insoluble in the monomer component are quickly transferred to solution upon contact with an aqueous medium. By this means, the monoperoxy dicarboxylic acid salt can exert its antiseptic effect rapidly as well. This is of particular significance for the use as bone cement. Despite modern hygiene and surgical techniques, there still is a certain level of infections in bone and/or soft tissues surrounding the articular endoprosthesis. In this context, a distinction between early and late infections is being made. Early infections are often caused by pathogens that enter the human tissue during the implantation of the articular endoprosthesis. Is therefore crucially important during this phase of the treatment that the antiseptic agent can exert its effect rapidly. Accordingly, powdered or particulate monoperoxy dicarboxylic acid salts with the smallest possible particle sizes are preferred.

In an embodiment 8 according to the invention, the composition is designed according to any one of the embodiments 1 to 7, whereby the salt of the monoperoxy dicarboxylic acid cannot be degraded by a peroxidase, preferably cannot be degraded by the catalase enzyme, within a period of 5 min in aqueous solution at room temperature.

The monoperoxy dicarboxylic acids and the salts thereof are not degraded for at least 5 min by the catalase enzyme or any other peroxidase. Preferably, the degradation does not take place within 10 min, particularly preferably does not take place within 20 min. In this context, "not degraded" shall be understood to mean that at least 80% of the originally used [amount of] monoperoxy dicarboxylic acid compound are still detectable after the specified time interval after the initial contact with an aqueous or water-containing solution or an aqueous medium, in particular body fluid.

According to the invention, the term, "room temperature", shall be understood to mean a temperature of 23° C. Accordingly, the monoperoxy dicarboxylic acid salts are not degraded by a peroxidase, preferably are not degraded by catalase enzyme, for 5 min at 23° C. A person skilled in the art is aware that enzymes usually have higher activity at higher temperatures and correspondingly lower activity at lower temperatures. Accordingly, the degradation of the monoperoxy dicarboxylic acid salt in the composition after contact with an aqueous medium may take place faster at temperatures above room temperature and may take place correspondingly slower at temperatures below room temperature.

In contrast to hydrogen peroxide, hydrogen peroxide adducts or comparable antiseptic hydrogen peroxide compounds, the degradation of monoperoxy dicarboxylic acids or salts thereof in the tissue by the action of peroxidases, in particular catalase, surprisingly takes place with a significant time delay. Presumably, the monoperoxy dicarboxylic acids are not degraded directly by catalase or other peroxidases, since these compounds do not comprise the corresponding substrate structure to undergo a direct interaction with the active centre of the corresponding enzyme. Moreover, the monoperoxy dicarboxylic acid is also presumed to be decomposed in a slow hydrolysis reaction forming hydrogen peroxide and the corresponding dicarboxylic acid upon contact with an aqueous medium. Only the hydrolysis product, i.e., hydrogen peroxide, is amenable to the degradation reaction by catalase. Therefore, presumably a longer-lasting and therefore improved antiseptic efficacy is attained by the monoperoxy dicarboxylic acids according to the invention or their pharmacologically tolerable salts as compared to the aforementioned hydrogen peroxide compounds. In this context, the effective antiseptic agents presumably are both the monoperoxy dicarboxylic acid compound used and the hydrolysis product, i.e., hydrogen peroxide.

In an embodiment 9 according to the invention, the composition is designed according to any one of the embodiments 1 to 8, whereby it contains 0.5% by weight to 6.0% by weight of the salt of the monoperoxy dicarboxylic acid, relative to the total amount of the composition.

To adjust the released amount of hydrogen peroxide as desired, the composition, in particular the bone cement, can contain a monoperoxy dicarboxylic acid salt fraction of 0.5 to 6.0% by weight, in particular 1.5 to 5% by weight, preferably from 2 to 4.5% by weight, more preferably between 3.0 and 4.0% by weight, relative to the total amount of the composition. In this context, the composition can just as well be produced by mixing two or more pastes or a paste and a powder component, whereby the monoperoxy dicarboxylic acid salt can be present in one or both pastes and just as well in the powder composition. It is preferred in this context that the content of the monoperoxy dicarboxylic acid salt present in the composition corresponds to a content of 0.5 to 6% by weight after a curing.

In an embodiment 10 according to the invention, the compositions design according to any one of the embodiments 1 to 9, whereby the monoperoxy dicarboxylic acid is selected from at least one element of the group of monoperoxy phthalic acid, monoperoxy glutaric acid, monoperoxy succinic acid, and monoperoxy cyclohexyldicarboxylic acid.

Preferably, the monoperoxy dicarboxylic acid is selected from the group of monoperoxy phthalic acid, monoperoxy glutaric acid, monoperoxy succinic acid, and monoperoxy cyclohexyldicarboxylic acid or a mixture of at least 2 of the aforementioned monoperoxy dicarboxylic acids.

In an embodiment 11 according to the invention, the composition is designed according to embodiment 10, whereby the monoperoxy dicarboxylic acid is monoperoxy phthalic acid.

In an embodiment 12 according to the invention, the composition is designed according to either one of the embodiments 10 or 11, whereby composition comprises the magnesium salt of monoperoxy phthalic acid.

It is preferred to select phthalic acid for the composition as monoperoxy dicarboxylic acid and particularly preferred to select the magnesium salt thereof. "Phthalic acid" shall be understood to mean ortho-phthalic acid or 1,2-benzenedicarboxylic acid.

The salts of aromatic monoperoxy dicarboxylic acids are more stable than the salts of aliphatic or alicyclic monoperoxy dicarboxylic acids. Moreover, the salts of unsubstituted aromatic peroxycarboxylic acids are less stable than phthalic acid, since the latter comprises an electron-withdrawing substituent that stabilises the peroxycarboxyl function. By this means, monoperoxyphthalic acid decomposes less easily to phthalic acid while releasing oxygen. The magnesium salt of monoperoxy phthalic acid is stable on storage and is commercially available inexpensively in technically relevant quantities.

In an embodiment 13 according to the invention, the composition is design according to any one of the embodiments 1 to 12, whereby the composition comprises at least one monomer for radical polymerisation and at least one organic polymer, whereby the polymer is soluble in said monomer.

A polymer that is soluble in the at least one monomer for radical polymerisation shall be understood to be a polymer of which at least 10 g/l, preferably at least 25 g/l, particularly preferably at least 50 g/l, and even more particularly preferably at least 100 g/l dissolve in said monomer for radical polymerisation. The polymer that is soluble in the polymerisable monomer can be a homopolymer or a copolymer. Said soluble polymer preferably is a polymer with a mean (by weight) molar mass (Mw) of at least 150,000 g/mol, in particular at least 200,000 g/mol and up to more than or equal to 500,000 g/mol.

The amount of the polymer that is soluble in said monomer for radical polymerisation that is present in the composition according to the invention usually is in a range of 1 to 85% by weight, relative to the total weight of the composition according to the invention. Accordingly, the polymer content of the following pastes A and/or B, and of powder component C and/or monomer component D can, independent of each other, be 1 to 85% by weight relative to the respective total composition of paste, powder component or monomer component.

In an embodiment 14 according to the invention, the composition is designed according to any one of the embodiments 1 to 13, whereby the organic polymer is selected from poly(alkyl-2-acrylic acid alkylester), poly(aryl-2-acrylic acid alkylester), poly(arylalkyl-2-acrylic acid alkylester), each independently having 1 to 20 C atoms in the alkyl group, each independently having 6 to 14 C atoms in the aryl group, each independently having 6 to 14 C atoms in the arylalkyl group, and each independently having 1 to 10 C atoms in the alkylester group or a mixture comprising at least two of said polymers.

The compositions according to the invention are bone cements comprising at least one organic polymer or mixtures of organic polymers, which are soluble in the monomers, whereby the polymers are polyacrylates. The organic polymer is selected, in particular, from poly(alkyl-2-acrylic acid alkylester), poly(aryl-2-acrylic acid alkylester), poly(arylalkyl-2-acrylic acid alkylester), each independently having 1 to 20 C atoms, preferably 1 to 18 C atoms in the alkyl group, in particular having 1 to 4 C atoms, each independently having 6 to 13 C atoms in the aryl group, in particular having 6, 10, 12 or 13 C atoms, each independently having 6 to 14 C atoms in the arylalkyl group, in particular having 8 to 12 C atoms, and each independently having 1 to 10 C atoms in the alkylester group, in particular having 1 to 4 C atoms, or a mixture comprising at least two of said polymers.

In an embodiment 15 according to the invention, the composition is designed according to any one of the embodiments 1 to 14, whereby the organic polymer is selected from the group of poly(methacrylic acid methylester), poly(methacrylic acid ethylester), poly(methylmethacrylic acid propylester), poly(methacrylic acid isopropylester), poly(methylmethacrylate-co-methylacrylate), poly(styrene-co-methylmethacrylate), copolymers of said compounds, and a mixture comprising at least two of said polymers, whereby polymethylmethacrylate (PMMA) is used particularly preferably.

The amount of the polymer that is soluble in said monomer for radical polymerisation that is present in the composition according to the invention usually is in a range of 1 to 85% by weight, relative to the total weight of the composition according to the invention. Accordingly, the polymer content of the following pastes A and/or B, and of powder component C and/or monomer component D can, independent of each other, be 1 to 85% by weight relative to the respective total composition of paste, powder component or monomer component.

At least one poly(methacrylic acid methylester) (PMMA) and methacrylic acid methylester (MMA) are used as particularly preferred organic polymer and as monomer, respectively, whereby mixtures thereof including further monomers or a copolymer of PMMA can be used just as well.

Polymers, in particular polyacrylates, having a molecular weight (MW) of preferably more than or equal to 200,000 g/mol are used as polymers that are soluble in the monomers for producing powder components, whereby molecular weights of more than or equal to 500,000 g/mol are preferred. Polymers having a molecular weight of less than or equal to 500,000 g/mol can also be used in pastes. In this context, the suitable molecular weight is determined, on the one hand, by whether a paste or a powder component is being produced and by the further components present in the paste, and by the polymer having to be soluble in the monomer that is used.

In an embodiment 16 according to the invention, the composition is designed according to any one of the embodiments 1 to 15, whereby the monomer is selected from at least one 2-alkyl-acrylic acid alkylester, 2-aryl-acrylic acid alkylester, 2-arylalkyl-acrylic cid alkylester, each independently having 1 to 20 C atoms in the alkyl group, each independently having 6 to 14 C atoms in the aryl group, each independently having 6 to 14 C atoms in the arylalkyl group, and each independently having 1 to 10 C atoms in the alkylester group or a mixture comprising at least two of said monomers.

In this context, the alkyl ester group can comprise a linear, branched or cyclical alkyl group, in particular having 1 to 4 C atoms.

Methacrylic acid methylester, a methacrylic acid ester or an alkylacrylic acid methylester are preferred in this context. Methacrylic acid methylester, such as a methacrylate monomer, in particular a methacrylate monomer that is liquid at a temperature of 25° C. and a pressure of 1,013 hPa, is particularly preferred. Preferably, the monomer for radical polymerisation is not a bisphenol A-derived methacrylic acid ester.

Preferably, the methacrylate monomer is a methacrylic acid ester. Preferably, the methacrylic acid ester is a monofunctional methacrylic acid ester. Preferably, said substance is hydrophobic. The use of hydrophobic mono-functional methacrylic acid esters allows later increases in bone cement volume due to the uptake of water and thus damage to the bone to be prevented. According to a preferred embodiment, the monofunctional methacrylic acid ester is hydrophobic if it contains no further polar groups aside from the ester group. The monofunctional hydrophobic methacrylic acid ester preferably comprises no carboxyl groups, hydroxyl groups, amide groups, sulfonic acid groups, sulfate groups, phosphate groups or phosphonate groups.

The monomer for radical polymerisation used according to the invention preferably has a molar mass of less than 1,000 g/mol. This also comprises monomers for radical polymerisation that are components of a mixture of monomers, whereby at least one of the monomers for radical polymerisation of the mixture of monomers has a defined structure with a molar mass of less than 1,000 g/mol.

The monomer for radical polymerisation is preferably characterised in that an aqueous solution, preferably one to which the monomer for radical polymerisation was added 1:1, has a pH in the range of 5 to 9, preferably in the range of 5.5 to 8.5, even more preferably in the range of 6 to 8, and particularly preferably in the range of 6.5 to 7.5.

According to a particularly preferred embodiment, the methacrylate monomer is methacrylic acid methylester, methacrylic acid ethylester or a mixture of said two monomers.

In an embodiment 17 according to the invention, the composition is designed according to any one of the embodiments 1 to 16, whereby the organic polymer comprises at least one poly(methacrylic acid methylester), (PMMA) or a poly(methacrylic acid methylester-copolymer), and methacrylic acid methyl ester (MMA) as monomer. Mixtures of these and further monomers can also be used in this context.

Also a subject matter of the invention are compositions comprising a particulate inorganic additive, in particular one having a BET surface of at least 40 $m^2/g$, whereby the additive preferably comprises covalently bound hydroxyl groups. Particulate inorganic additives that are suitable according to the invention comprise HO—Si groups that are covalently bound to the particles (silanol groups). Said hydroxyl groups that are arranged on the surface of the particles allow hydrogen bonds between the filling agent particles to form, which can be released reversibly through the action of mechanical or thermal energy.

The particulate inorganic additive is preferably selected from the group of pyrogenic silicon dioxide, pyrogenic mixed metal-silicon oxides, bentonite, montmorillonite, and a mixture containing at least two of said additives.

Moreover, it is also feasible to use pyrogenic silicon dioxide made hydrophobic. The hydrophobic silicon dioxide can be produced according to the prior art through treating pyrogenic silicon dioxide with dialkyldichlorosilanes (e.g., dimethyldichlorosilane).

Pyrogenic silicon dioxide with a BET surface of at least 40 $m^2/g$, particularly preferably of 200 $m^2/g$, and most preferably of 300 $m^2/g$, is a particularly preferred particulate inorganic filling agent. Said pyrogenic silicon dioxide is commercially available by the brand name of Aerosil® having specific BET surfaces of 50 $m^2/g$, 90 $m^2/g$, 200 $m^2/g$, and 380 $m^2/g$.

Pyrogenic silicon oxide having a BET surface of at least 200 $m^2/g$ is particularly preferred as particulate inorganic additive. It is also preferred to use, as particulate inorganic additive, a pyrogenic silicon dioxide having a BET surface of at least 300 $m^2/g$. The particulate inorganic additives that are suitable according to the invention preferably comprise primary particles of approx. 7 nm having a specific surface of 270 to 330 $m^2/g$.

The BET measurement is an analytical procedure for characterisation of surfaces of solid bodies by means of gas adsorption. Said determination method is described in DIN ISO 9277:2003-05 (Determination of the specific surface of solids by gas adsorption according to the BET method).

A composition according to the invention comprises, aside from the soluble organic polymer, in particular polymethylmethacrylate (PMMA), and the monomer for radical polymerisation, in particular methacrylic acid methylester, a particulate inorganic additive, preferably at a concentration from 0.01 to 0.5% by weight, in particular from 0.01 to 0.25% by weight, preferably from 0.02-0.14% by weight relative to the total composition. According to the invention, the cement dough produced by mixing the powder component and the liquid monomer component comprises the particulate inorganic additive at a concentration from 0.01-0.14% by weight.

In addition to the aforementioned components, a composition according to the invention comprises a radiopaquer, a polymerisation initiator and/or a polymerisation accelerator as well as, optionally, in addition, filling agents that are different from the additive and simply show a thickening effect, such as, for example, silicon dioxide having a BET surface of clearly less than 35 $m^2/g$.

A contribution to meeting at least one of the objects according to the invention is provided by a kit 1, comprising a paste A and a paste B, whereby (a) paste A contains (a1) at least one monomer for radical polymerisation, in particular 15 to 85% by weight thereof, preferably 20 to 70% by weight thereof, more preferably 25 to 60% by weight thereof, particularly preferably 25 to 50% by weight thereof;

(a2) at least one organic polymer that is soluble in (a1), in particular 5 to 50% by weight thereof, preferably 10 to 40% by weight thereof, particularly preferably 20 to 30% by weight thereof; and (a3) optionally, at least one polymerisation inhibitor, in particular 0.05 to 1.0% by weight thereof; and (a4) at least one component of a redox initiator system, in particular 0.1 to 10% by weight thereof, preferably 0.01 to 8% by weight thereof, particularly preferably 0.01 to 5% by weight thereof;

as well as, optionally, further components, such as radiopaquer and/or filling agent that is insoluble in (a1), each relative to the total weight of paste A; and (b) paste B contains (b1) at least one monomer for radical polymerisation, in particular 15 to 85% by weight thereof, preferably 20 to 70% by weight thereof, more preferably 25 to 60% by weight thereof, particularly preferably 25 to 50% by weight thereof;

(b2) at least one organic polymer that is soluble in (b1), in particular 5 to 50% by weight thereof, preferably 10 to 40% by weight thereof, particularly preferably 20 to 30% by weight thereof; and (b3) at least one polymerisation accelerator, in particular 0.0005 to 0.5% by weight thereof, as well as, optionally, further components, radiopaquer and/or filling agent that is insoluble in (b1), each relative to the total weight of paste B, and whereby at least one of the pastes A or B contains, as component (a5) or (b4), or both pastes A and B contain, as components (a5) and (b4), at least a content of a pharmacologically tolerable salt of a monoperoxy dicarboxylic acid, in particular 0.5 to 6.0% by weight thereof, preferably 1.5 to 5% by weight thereof, particularly preferably from 2 to 4.5% by weight thereof, more preferably between 3.0 to 4.0% by weight thereof, relative to the total amount of the composition.

In this context, each of the pastes can contain the particulate inorganic additive at a concentration of 0.001 to 2% by weight, in particular 0.001 to 1% by weight, such that 0.01 to 0.5% by weight of the additive, in particular from 0.01 to 0.25% by weight, preferably 0.02-0.14% by weight, relative to the total composition, can be present in the composition that can be obtained through mixing pastes A and B, in particular at a ratio of approximately 1 to 1 plus/minus 0.5 in either value.

The same applies in like manner to the following powder component C and paste D.

The monomers and polymers defined above are used as monomers and polymers in pastes A and B. The same applies in like manner to the following powder component C and paste D.

A contribution to meeting at least one of the objects according to the invention is made by a kit 2, comprising a powder component C and a liquid monomer component D, whereby (c) powder component C contains (c1) at least one powdered poly(meth)acrylate, in particular 1 to 95% by weight thereof, preferably up to 85% by weight, and particularly preferably 50 to 80% by weight;

(c2) at least one powdered radiopaquer, in particular 3 to 60% by weight thereof, preferably 3 to 30% by weight thereof, particularly preferably from 5 to 15% by weight thereof; and (c3) at least one polymerisation initiator, in particular 0.01 to 10% by weight thereof, preferably 0.01 to 8% by weight thereof, particularly preferably 0.01 to 5% by weight thereof, further preferably 0.4 to 3.0% by weight thereof, as well as, optionally, further components such as powdered filling agent, each relative to the total weight of powder component C; and (d) monomer component D contains (d1) at least one monomer for radical polymerisation, in particular 80 to 99.9995 percent by weight thereof, preferably from 80 to 99% by weight thereof;

(d2) optionally, at least one polymerisation inhibitor, in particular 0.1 to 1.5% by weight thereof;

(d3) optionally, at least one organic polymer that is soluble in (d1), in particular up to 19% by weight thereof; and (d4) at least one polymerisation accelerator, in particular 0.0005 to 1.5% by weight thereof, preferably 0.1 to 1.5% by weight thereof, as well as, optionally, further components, such as radiopaquer and/or filling agent that is insoluble in (d1) and/or additive, each relative to the total weight of monomer component D, and whereby powder component C contains, as component (c4), a content of a pharmacologically tolerable salt of a monoperoxy dicarboxylic acid, in particular 0.5 to 6.0% by weight thereof, preferably 1.5 to 5% by weight thereof, particularly preferably from 2 to 4.5% by weight thereof, more preferably between 3.0 to 4.0% by weight thereof, relative to the total amount of the composition.

According to the invention, a kit shall be understood to be a system made up of at least two components. Although reference to two components (e.g., paste A and paste B) is made in the following, the kit can just as well contain more than two components, for example three, four, five or more than five components, according to need. The individual kit components preferably are provided to be packaged separate from each other such that the ingredients of the one kit component do not contact the ingredients of another kit component. Accordingly, it is feasible, for example, to package the respective kit components separate from each other and to store them together in a reservoir container.

Preferably, the kit is appropriately designed as a device for producing compositions for use as bone cement such that it comprises a first container and a second container, whereby the first container comprises, for example, paste A and the second container comprises paste B, whereby at least one of the containers can be opened to allow paste A and paste B to be mixed after the opening, and a mixing unit for the mixing of pastes A and B.

Referring to kit 1, for this purpose, the at least two pastes A and B are mixed with each other, upon which the composition according to the invention is obtained. The mixing ratio preferably is 0.5 to 1.5 parts by weight of paste A and 0.5 to 1.5 parts by weight of paste B. According to a particularly preferred embodiment, the fraction of paste A is 30 to 70% by weight and the fraction of paste B is 30 to 70% by weight, each relative to the total weight of pastes A and B, respectively.

After the pastes of kit 1 are mixed, the composition that is ultimately obtained is tack-free in accordance with the ISO 5833 standard after no more than 1 to 2 minutes.

In case of kit 2, the mixing ratio of powder component C and monomer component D preferably ranges from 3 to 1 to 1 to 2, in particular is 2 to 1 parts by weight. The mixing process can involve common mixing devices, for example a static mixer or a dynamic mixer. Accordingly, kit 2 as a device for producing the composition according to the invention can comprise a first container for powder component C and a second container for monomer component D.

It is preferable to use the aforementioned compounds as pharmacologically tolerable monopreoxy dicarboxylic acid salts in either one of the pastes A and/or B or, alternatively, of the powder component C in the specified amounts, each relative to 100% by weight of the total composition.

An organic polymer in the form of a powder according to the preceding definition is used as powdered poly(meth)acrylate, whereby powdered PMMA is preferred. In general, an additive content can be present both in the powder component and in the paste.

In the case of a composition according to the invention that was obtained by combining two pastes A and B or powder component C and monomer component D of a two-component system, said composition preferably contains at least one polymerisation initiator (that was present in the one paste/component of the two-component system) and at least one polymerisation accelerator (that was present in the other paste/component of the two-component system).

Usually, paste A and/or B and powder component C and/or monomer component D contain a radiopaquer, each independent of each other.

The above-mentioned pastes A and B can be mixed with each other at any arbitrary ratio, whereby the use of pastes A and B at a ratio of essentially 1:1 for mixing has proven to be preferred, whereby the ratio can vary by plus/minus 50% independent of each other.

The compositions, pastes and/or powder components according to the invention can contain at least one polymerisation initiator (which preferably is soluble in the monomer for radical polymerisation), at least one polymerisation accelerator (which preferably is soluble in the monomer for radical polymerisation), at least one co-polymerisation accelerator, if applicable, or at least one co-polymerisation initiator, if applicable.

In the case of a one-component system being the composition according to the invention, the polymerisation initiator preferably is an activatable polymerisation initiator, e.g., a photoinitiator that is dissolved or suspended in the composition, which is present as a paste, or a photoinitiator system that is dissolved or suspended in the paste. It is feasible just as well to provide an initiator or initiators where it/they are temporarily in contact with the paste, for example in a container part, a dosing facility or a transport cannula.

Moreover, in a one-component system, the composition or paste according to the invention can also contain an electrically conductive radiopaquer aside from the activatable polymerisation initiator. Particles made of cobalt, iron, NdFeB, SmCo, cobalt-chromium steel, zirconium, hafnium, titanium, titanium-aluminium-silicon alloys, and titanium-niobium alloys having a particle size of 0.5-500 µm are particularly well-suited in this context. It is feasible to induce eddy currents in said electrically conductive radiopaquer through alternating magnetic fields with a frequency in the range of 500 Hz to 50 kHz which cause the opaquer to heat up. Due to heat transmission, the initiator is heated as well and induced to thermally disintegrate.

A contribution to meeting at least one of the objects according to the invention is made by an embodiment 1 of a curable bone cement, whereby the bone cement can be obtained by polymerisation of a composition according to the invention according to any one of the embodiments 1 to 17. Another contribution to meeting at least one of the objects according to the invention is made by an embodiment 2 of a curable bone cement, whereby the bone cement can be obtained by mixing pastes A and B from kit 1. Another contribution to meeting at least one of the objects according to the invention is made by an embodiment 3 of a curable bone cement, whereby the bone cement can be obtained by mixing and polymerizing powder component C and monomer component D from kit 2.

In this context, the curable bone cement has a content of pharmacologically tolerable monoperoxy dicarboxylic acid salt of, in particular, 0.5 to 6.0% by weight, preferably 1.5 to 5% by weight, particularly preferably from 2 to 4.5% by weight, and more preferably between 3.0 to 4.0% by weight, relative to the total composition.

A contribution to meeting at least one of the objects according to the invention is made by an embodiment 1 of a curable bone cement that can be obtained by polymerisation of a composition according to any one of the embodiments 1 to 17. Another contribution to meeting at least one of the objects according to the invention is made by an embodiment 2 of a curable bone cement that can be obtained by mixing and polymerising pastes A and B from kit 1. Another contribution to meeting at least one of the objects according to the invention is made by an embodiment 3 of a curable bone cement that can be obtained by mixing and polymerising powder component C and monomer component D from kit 2.

In this context, the cured bone cement has a content of pharmacologically tolerable monoperoxy dicarboxylic acid salt of, in particular, 0.5 to 6.0% by weight, preferably 1.5 to 5% by weight, particularly preferably from 2 to 4.5% by weight, and more preferably between 3.0 to 4.0% by weight, relative to the total composition.

Preferably, the pharmacologically tolerable monoperoxy dicarboxylic acid salt is released or is only then releasable from the curable or cured composition only in the presence of water, moist or aqueous conditions, particularly preferably only after the curing.

A contribution to meeting at least one of the objects according to the invention is therefore also made by an embodiment 4 of a cured bone cement according to any one of the embodiments 1 to 3, whereby the salt of the monoperoxy dicarboxylic acid is dissolved from the composition in the presence of water during the curing and the monoperoxy dicarboxylic acid is not degraded within 5 min by a peroxidase, preferably is not degraded by the catalase enzyme.

A contribution to meeting at least one of the objects according to the invention is also made by an embodiment 1 of a form body that can be obtained by polymerisation of a composition according to any one of the embodiments 1 to 17. Another contribution to meeting at least one of the objects according to the invention is also made by an embodiment 2 of a form body that can be obtained by mixing and subsequently polymerising pastes A and B from kit 1. Another contribution to meeting at least one of the objects according to the invention is also made by an embodiment 3 of a form body that can be obtained by mixing and subsequently polymerising powder component C and monomer component D from kit 2.

In this context, the form body has a content of pharmacologically tolerable monoperoxy dicarboxylic acid salt of, in particular, 0.5 to 6.0% by weight, preferably 1.5 to 5% by weight, particularly preferably from 2 to 4.5% by weight, and more preferably between 3.0 to 4.0% by weight, relative to the total form body.

A contribution to meeting at least one of the objects according to the invention is also made through a use of a composition according to any one of the embodiments 1 to 17 or a use 2 of kit 1 or a use 3 of kit 2 as implant, as antiseptic implant, as revision implant, for mechanical fixation of primary total articular endoprostheses, for mechanical fixation of revision total articular endoprostheses, for augmentation of osteoporotic bone tissue and, particularly preferably, for vertebroplasty, kyphoplasty, and augmentation of drill holes in osteoporotic bone tissue, for filling bone cavities, for femuroplasty, for the manufacture of spacers, for mechanical fixation of articular endoprostheses, for covering skull defects or for the production of carrier materials for local antibiotics therapy or as carrier material for local release of pharmaceutically active substances.

Conceivable as polymerisation initiator are, in particular, peroxides and barbituric acid derivatives, whereby preferably at least 1 g/l, more preferably at least 3 g/l, even more preferably at least 5 g/l, and particularly preferably at least 10 g/l of the peroxides and barbituric acid derivatives can dissolve in the polymerisable monomer at a temperature of 25° C. The polymerisation initiators disintegrate through radical reactions, usually while forming hydrogen radicals and cleaving off oxygen. The initiator does not form hydrogen peroxide in the presence of water. Cumene hydroperoxide can become rearranged in the presence of water to form ketone and phenol. Radicals such as H—O—O•, R—O—O•, R=organic residue, are not considered to be hydrogen peroxide.

In terms of the polymerisation initiator, a peroxide is understood to mean compounds that contain at least one peroxo group (—O—O—). The peroxide preferably comprises no free acid groups. The peroxide can be an inorganic peroxide or an organic peroxide, such as, for example, a toxicologically acceptable hydroperoxide. However, the hydroperoxide is not a hydrogen peroxide. According to a particularly preferred embodiment, the peroxide is selected from the group consisting of cumene-hydroperoxide, 1,1,3,3-tetramethylbutyl-hydroperoxide, t-butyl-hydroperoxide, t-amyl-hydroperoxide, di-isopropylbenzen-mono-hydroperoxide, and a mixture of at least thereof.

The barbituric acid derivative preferably is a barbituric acid derivative selected from the group consisting of 1-mono-substituted barbiturates, 5-mono-substituted barbiturates, 1,5-di-substituted barbiturates, and 1,3,5-tri-substituted barbiturates. According to a particular refinement of the paste according to the invention, the barbituric acid derivative is selected from the group consisting of 1,5-di-substituted barbiturates and 1,3,5-tri-substituted barbiturates.

There is no limitation with regard to the type of substituents on the barbituric acid. The substituents can, for example, be aliphatic or aromatic substituents. In this context, alkyl, cycloalkyl, allyl or aryl substituents can be preferred. The substituents can also bear hetero atoms. In particular, the substituents can be thiol substituents. Accordingly, 1,5-disubstituted thiobarbiturates or 1,3,5-trisubstituted thiobarbiturates can be preferred. According to a preferred embodiment, the substituents each have a length of 1 to 10 carbon atoms, more preferably a length of 1 to 8 carbon atoms, and particularly preferably a length in the range of 2 to 7 carbon atoms.

According to the invention, barbiturates bearing one substituent each at position 1 and position 5 or one substituent each at positions 1, 3, and 5 are preferred. According to another preferred embodiment, the barbituric acid derivative is a 1,5-disubstituted barbiturate or a 1,3,5-trisubstituted barbiturate. According to a particularly preferred embodiment, the barbituric acid derivative is selected from the group consisting of 1-cyclohexyl-5-ethyl-barbituric acid, 1-phenyl-5-ethyl-barbituric acid, and 1,3,5-trimethyl-barbituric acid.

Heavy metal compounds selected from the group consisting of heavy metal salts and heavy metal complexes are preferred as polymerisation accelerator. Heavy metal compounds that are preferred according to the invention are selected from the group consisting of copper(II) hydroxide, copper(II) methacrylate, copper(II) acetylacetonate, copper(II)-2-ethyl-hexanoate, cobalt(II) hydroxide, cobalt(II)-2-ethyl-hexanoate, basic copper(II) carbonate, iron(II)-2-ethyl-hexanoate, iron(III)-2-ethyl-hexanoate, and a mixture of at least two thereof.

According to another refinement of the composition or paste according to the invention, the polymerisation accelerator is selected from the group consisting of N,N-dimethyl-p-toluidine, N,N-bis-hydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, and 1,5-diazabicyclo(4.3.0)non-5-ene, phthalimide, maleimide, succinimide, pyromellitic acid diimide, and a mixture of at least two thereof.

Another advantageous refinement of the invention comprises the use, as polymerisation accelerator, of combinations of heavy metal salts and at least one member of the group comprising N,N-dimethyl-p-toluidine, N,N-bis-hydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, and 1,5-diazabicyclo(4.3.0)non-5-ene, phthalimide, maleimide, succinimide, and pyromellitic acid diimide. In this context, combinations of two and combinations of three different polymerisation accelerators are disclosed in the scope of the invention.

An advantageous refinement of the invention is that the composition according to the invention or any of the pastes A, B or monomer component D contains at least one co-polymerisation accelerator, if applicable, whereby tertiary amines and amidines are preferred as co-polymerisation accelerators, and whereby N,N-dimethyl-p-toluidine, N,N-bis-hydroxyethyl-p-toluidine, N,N-dimethyl-aniline, 1,8-diazabicyclo[5.4.0-]undec-7-ene, and 1,5-diazabicyclo(4.3.0)-non-5-ene are particularly preferred as co-accelerators.

The composition according to the invention, in particular in a paste or monomer component, can contain a (total) amount of the polymerisation initiator, polymerisation accelerator, co-polymerisation accelerator or the polymerisation initiator, polymerisation accelerator, and co-polymerisation accelerator of up to 10% by weight, relative to the total weight of the composition according to the invention or, each independent of each other, relative to the total weight of any of the pastes A, B or monomer component D.

The composition according to the invention and, in particular, pastes A and B as well as monomer component D and powder component C can contain further ingredients aside from the afore-mentioned components.

According to a preferred embodiment of the composition according to the invention or of any of the pastes A, B and monomer component D or powder component C, these can, each independent of each other, contain at least one radiopaquer. The radiopaquer can be a common radiopaquer in this field. Suitable radiopaquers can be soluble or insoluble in the monomer for radical polymerisation. The radiopaquer is preferably selected from the group consisting of metal oxides (such as, for example, zirconium dioxide), barium sulfate, toxicologically acceptable heavy metal particles (such as, for example, tantalum), ferrite, magnetite (supramagnetic magnetite also, if applicable), and biocompatible calcium salts. Said radiopaquers preferably have a mean particle diameter in the range of 10 nm to 500 μm. Moreover, conceivable radiopaquers also include esters of 3,5-bis(acetamido)-2,4,6-triiodobenzoic acid, gadolinium compounds, such as gadolinium chelate involving the esters of 1,4,7,10- tetraazacyclododecane-1,4,7,10-tetraacetic acid (DOTA). The radiopaquer concentrations, in particular the zirconium dioxide concentration, in the composition according to the invention or any of the pastes A or B and powder component C or monomer component D can, each independent of each other, be in a range of, for example, 3 to 30% by weight relative to the corresponding total composition. Radiopaquers are not considered to be filling agents herein.

According to a further preferred embodiment, the composition according to the invention or any of the pastes specified above can contain at least one colourant. The colourant can be a common colourant in this field and preferably can be a food colourant. Moreover, the colourant can be soluble or insoluble in the at least one monomer for radical polymerisation. According to a particularly preferred embodiment, the colourant is selected from the group consisting of E101, E104, E132, E141 (chlorophyllin), E142, riboflavin, and lissamine green. According to the invention, the term, colourant, shall also include colour varnishes, such as, for example, colour varnish green, the aluminium salt of a mixture of E104 and E132.

According to a further preferred embodiment, the composition according to the invention can contain at least one biocompatible elastomer. Preferably, the biocompatible elastomer is particulate. Preferably, the biocompatible elastomer is soluble in the at least one monomer for radical polymerisation. The use of polybutadiene as biocompatible elastomer has proven to be particularly well-suited.

According to a further preferred embodiment, the composition according to the invention can contain at least one monomer having adsorption groups. An adsorption group can, for example, be an amide group. Accordingly, the monomer with adsorption group can, for example, be methacrylic acid amide. Using at least one monomer with adsorption groups allows the binding of the bone cement to articular endoprostheses to be influenced specifically.

According to a further preferred embodiment, the composition according to the invention or at least one of the pastes A, B or monomer component D can contain at least one polymerisation inhibitor, also called stabiliser. The polymerisation inhibitor shall be suitable to prevent spontaneous polymerisation of the monomers for radical polymerisation contained in the paste. Moreover, the polymerisation inhibitor shall not undergo interfering interactions with the other ingredients contained in the paste according to the invention. Polymerisation inhibitors of said type are known from the prior art. According to a preferred embodiment, the stabiliser is 2,6-di-tert-butyl-4-methylphenol and/or 2,6-di-tert-butyl-phenol.

The invention is illustrated in more detail through the examples presented in the following, though without limiting the scope of the invention.

EXAMPLES 1-5

Determination of the mechanical parameters in accordance with ISO 5833

The cement powders shown in the Table below are produced using 75% dibenzoylperoxide as polymerisation initiator (BPO, phlegmatised with 25% by weight water, procured from Akzo Nobel, batch no. 2612211601), magnesium monoperoxy-o-phthalate-hexahydrate as monoperoxy dicarboxylic acid salt (technical grade, content approximately 80%, procured from Sigma Aldrich, product no. 69868, particle size<250 µm), zirconium dioxide as radiopaquer (procured from S. Goldmann, batch no. FB100856) and poly(methylmethacrylate-co-methylacrylate) (PMMA-co-MA, procured from Evonik, batch no. 310HDF129) as copolymer component.

| | Composition/g | | | | |
|---|---|---|---|---|---|
| | Magnesium monoperoxy-o-phthalate (MMPP) | | | | |
| Example no. | MMPPx6H$_2$O (hexahydrate) | MMPP (pure substance) | PMM-co-MA (copolymer) | Zirconium dioxide | BPO |
| 1 (Reference example) | — | — | 33.41 | 6.0 | 0.59 |
| 2 | 0.63 | 0.50 | 33.41 | 6.0 | 0.59 |
| 3 | 1.25 | 1.00 | 33.41 | 6.0 | 0.59 |
| 4 | 1.88 | 1.50 | 33.41 | 6.0 | 0.59 |
| 5 | 2.50 | 2.00 | 33.41 | 6.0 | 0.59 |

Example 1 is a reference example containing no monoperoxy dicarboxylic acid salt.

Examples 2 to 5 are examples according to the invention.

According to the compositions given above, 40 g of powder component were used in example 1 (reference example), 40.63 g of powder component were used in example 2, 41 point to 5 g of powder component were used in example 3, 43.38 g of powder component were used in example 4, and 44.5 g of powder component were used in example 5.

A liquid monomer component (Heraeus Medical, batch no. 5271) of the following composition was used for the production of bone cement for the determination of the mechanical properties and antimicrobial efficacy: 98.0% by weight methylmethacrylate as monomer for radical polymerisation, 2.0% by weight N,N-dimethyl-p-toluidine as polymerisation accelerator, and 20 ppm p-hydroquinone as polymerisation inhibitor.

Production of Test Bodies

ISO 5833 requires a flexural strength of ≥50 MPa, a flexural modulus of ≥1,800 MPa, and a compressive strength of ≥70 MPa. Test bodies were produced in accordance with ISO 5833 for the test of the mechanical properties.

For this purpose, the cement powders according to the aforementioned compositions of examples 1 to 5 were mixed with 20 ml liquid monomer component each. This resulted, after approximately 60 seconds, in a tack-free, plastically deformable viscous cement dough that cured after few minutes. The cement dough of reference example 1 and inventive examples 2 to 5 was used to produce strip-shaped test bodies sized 75 mm×10 mm×3.3 mm for the test of the flexural strength and flexural modulus in accordance with ISO 5833. In addition, cylindrical test bodies (diameter 6 mm, height 12 mm) were manufactured for the compressive strength test.

After storage of the test bodies at 23° C. at a relative humidity of 50% for a period of 24 hours, the flexural strength, flexural modulus, and compressive strength were determined in accordance with ISO 5833 using a Zwick universal testing machine. The results are summarised in the Table below.

| Example no. | Flexural strength [MPa] ≥50 MPa | Flexural modulus [MPa] ≥1800 MPa | Compressive strength [MPa] ≥70 MPa |
|---|---|---|---|
| | Requirements according to ISO 5833 | | |
| 1 | 72.1 ± 1.5 | 2832 ± 43 | 99.7 ± 1.1 |
| 2 | 72.2 ± 3.1 | 2832 ± 31 | 100.3 ± 1.5 |
| 3 | 68.6 ± 2.9 | 2735 ± 46 | 99.4 ± 1.9 |
| 4 | 70.1 ± 2.7 | 2704 ± 30 | 98.8 ± 1.0 |
| 5 | 67.1 ± 2.7 | 2686 ± 47 | 99.4 ± 1.4 |

The results show that the mechanical requirements of ISO 5833 with regard to the flexural strength, flexural modulus, and compressive strength were met by the cements of reference example 1 as well as the inventive examples 2 to 5. Moreover, it was shown that the addition of the monoperoxy dicarboxylic acid salt does not have a detrimental influence on the radical polymerisation and that test bodies with comparable mechanical properties are obtained in examples 2 to 5.

Determination of the antimicrobial efficacy in the presence of the defibrinated sheep blood.

The antimicrobial efficacy was tested using the film contact method in line with JIS Z 2801 (Japanese industry standard). The cements of reference example 1 and inventive examples 2 to 5 were used to produce strip-shaped cement testing bodies sized 50 mm ×50 mm×3 mm, 3 test bodies from each example. The test bodies were disinfected on the surface using a 70% by weight aqueous ethanol solution. *Staphylococcus aureus* ATCC6538 was used as the test germ. The test germ was inoculated in 5% by weight blood solution (5% by weight defibrinated sheep blood in 0.9% aqueous sodium chloride solution). In each case, 0.2 ml of a suspension of the test germ at a concentration of 0.5-2.0× $10^6$ cfu/ml were applied to the surface of the test body. This resulted in a germ load of 1.0-4.0× $10^5$ cfu/ml. A plastic film was placed on the germ suspension such that the distance between the test body surface and the plastic film was proximately 100 µm. The inoculated test bodies were incubated in a steam-saturated atmosphere at 36±1° C. for 24 hours. Then the germs were detached in PE bags with 10 ml physiological saline each. The germ suspensions were plated on TSA plates (tripticase soy agar). The TSA plates were then incubated for 40-48 hours at 36±1° C. Then, the number of colonies produced was counted with a colony counter. The germ counts per test body were determined taking into consideration the dilution. The means of the germ counts of three test bodies from each example were determined and the reduction factor was calculated taking into consideration the reference samples.

Reduction factor (RF)=c−d whereby c: arithmetic mean of the $\log_{10}$ germ counts on the incubated test body surfaces d: arithmetic mean of the $\log_{10}$ germ counts on the incubated reference sample body surfaces

| Example no. | Reduction factor |
|---|---|
| 1 (reference example) | No reduction |
| 2 | 4.32 |
| 3 | >4.99 |
| 4 | >4.99 |
| 5 | >4.99 |

The cements of examples 2-5 show a significant reduction of the germ counts by 4 log units. This means that at least 99.99% of the test germs were killed.

Preferred refinements of components of one category according to the invention shall also be preferred for like or corresponding components of the respective other category according to the invention. The terms, "possessing", "comprising" or "including", etc., shall not exclude further elements, ingredients, etc., possibly being included. The indefinite article, "a", shall not exclude that a plurality may be present.

The invention claimed is:

1. A composition for use as a bone cement, the composition comprising a curable, pharmacologically tolerable mixture of a polymerizable monomer and a pharmacologically tolerable salt of a monoperoxy dicarboxylic acid, wherein the salt of the monoperoxy dicarboxylic acid can be dissolved from the composition in the presence of water.

2. Composition according to claim 1, wherein the composition is an antiseptic bone cement.

3. Composition according to claim 1, wherein the composition is an antiseptic polymethylmethacrylate bone cement.

4. Composition according to claim 1, wherein the salt of the monoperoxy dicarboxylic acid is in alkaline earth salt or an alkali salt.

5. Composition according to claim 4, wherein the alkaline earth salt is a magnesium salt.

6. Composition according to claim 1, wherein the salt of the monoperoxy dicarboxylic acid is not soluble in methylmethacrylate at room temperature.

7. Composition according to claim 1, wherein the salt of the monoperoxy dicarboxylic acid in the composition is used in the form of a powder, whereby the powder has a mean particle size of not more than 250 µm.

8. Composition according to claim 1, wherein the salt of the monoperoxy dicarboxylic acid is not degraded within 5 min by the catalase enzyme in aqueous solution at room temperature.

9. Composition according to claim 1, which contains 0.5% by weight to 6.0% by weight of the salt of the monoperoxy dicarboxylic acid, relative to the total amount of the composition.

10. Composition according to claim 1, wherein the monoperoxy dicarboxylic acid is selected from at least one element of the group of monoperoxy phthalic acid, monoperoxy glutaric acid, monoperoxy succinic acid, and monoperoxy cyclohexyldicarboxylic acid.

11. Composition according to claim 10, wherein the monoperoxy dicarboxylic acid is monoperoxy phthalic acid.

12. Composition according to claim 10, wherein the composition comprises the magnesium salt of monoperoxy phthalic acid.

13. Composition according to claim 1, wherein the composition comprises at least one monomer for radical polymerisation and at least one organic polymer, whereby the polymer is soluble in said monomer.

14. Composition according to claim 13, wherein the organic polymer is selected from poly(alkyl-2-acrylic acid alkylester), poly(aryl-2-acrylic acid alkylester), poly(arylalkyl-2-acrylic acid alkylester), each independently having 1 to 20 C atoms in the alkyl group, each independently having 6 to 14 C atoms in the aryl group, each independently having 6 to 14 C atoms in the arylalkyl group, and each independently having 1 to 10 C atoms in the alkylester group or a mixture comprising at least two of said polymers.

15. Composition according to claim 13, wherein the organic polymer is selected from the group of poly(methacrylic acid methylester), poly(methacrylic acid ethylester), poly(methylmethacrylic acid propylester), poly(methacrylic acid isopropylester), poly(methylmethacrylate-co-methylacrylate), poly(styrene-co-methylmethacrylate), copolymers of monomers making up said polymers, and a mixture of at least two of said polymers.

16. Composition according to claim 13, wherein the monomer is selected from at least one 2-alkyl-acrylic acid alkylester, 2-aryl-acrylic acid alkylester, 2-arylalkyl-acrylic acid alkylester, each independently having 1 to 20 C atoms in the alkyl group, each independently having 6 to 14 C atoms in the aryl group, each independently having 6 to 14 C atoms in the arylalkyl group, and each independently having 1 to 10 C atoms in the alkylester group or a mixture comprising at least two of said monomers.

17. Composition according to claim 13, wherein the organic polymer comprises at least one poly(methacrylic acid methylester) (PMMA), or a poly(methacrylic acid methylester-co-polymer), and methacrylic acid methylester (MMA) as monomer.

18. Kit 1, comprising a paste A and a paste B, whereby
(a) paste A contains:
(a1) at least one monomer for radical polymerisation;
(a2) at least one organic polymer that is soluble in (a1);
(a3) optionally, at least one polymerisation inhibitor; and
(a4) at least one component of a redox initiator system;
(b) paste B contains:
(b1) at least one monomer for radical polymerisation;
(b2) at least one organic polymer that is soluble in (b1); and
(b3) at least one polymerisation accelerator;
and whereby at least one of the pastes A or B contains, as component (a5) or (b4), a pharmacologically tolerable salt of a monoperoxy dicarboxylic acid.

19. Kit comprising a powder component C and a liquid monomer component D, whereby
(c) powder component C contains:
(c1) at least one powdered poly(meth)acrylate;
(c2) at least one powdered radiopaquer;
(c3) at least one polymerisation initiator;
(d) monomer component D contains:
(d1) at least one monomer for radical polymerisation;
(d2) optionally, at least one polymerisation inhibitor;
(d3) optionally, at least one organic polymer that is soluble in (d1); and
(d4) at least one polymerisation accelerator;
and whereby powder component C contains, as component (c4), a pharmacologically tolerable salt of a monoperoxy dicarboxylic acid.

20. Curable bone cement, obtained by polymerisation of a composition according to claim 1.

21. Cured bone cement, obtained by polymerisation of a composition according to claim 1, whereby the cured bone cement comprises a content of the pharmacologically tolerable salt of the monoperoxy dicarboxylic acid of 0.5% by weight to 6% by weight, relative to the total composition.

22. Cured bone cement according to claim 21, wherein the salt of the monoperoxy dicarboxylic acid is dissolved from the composition in the presence of water during the curing and the monoperoxy dicarboxylic acid is not degraded within 5 min by the catalase enzyme.

23. Form body, obtained by polymerisation of a composition according to claim 1.

24. Method of using a composition according to claim 1 as implant, antiseptic implant, as revision implant, for mechanical fixation of primary total articular endoprostheses, for mechanical fixation of revision total articular endoprostheses, for augmentation of osteoporotic bone tissue, for vertebroplasty, kyphoplasty, and augmentation of drill holes in osteoporotic bone tissue, for filling bone cavities, for femuroplasty, for the manufacture of spacers, for mechanical fixation of articular endoprostheses, for covering skull defects or for the production of carrier materials for local antibiotics therapy or as carrier material for local release of pharmaceutically active substances.

* * * * *